United States Patent [19]

Heidenfelder

[11] Patent Number: 4,840,188
[45] Date of Patent: Jun. 20, 1989

[54] DESENSITIZING CONDOM

[76] Inventor: Herbert J. Heidenfelder, 1270 NE. 95th St., Miami Shores, Fla. 33138

[21] Appl. No.: 142,647

[22] Filed: Jan. 11, 1988

[51] Int. Cl.⁴ ................................................. A61F 5/44
[52] U.S. Cl. ..................................... 128/844; 604/349
[58] Field of Search ............... 604/349, 350, 351, 352, 604/353; 128/79, 132 R, 830, 842–844; 116/200, 327

[56] References Cited

U.S. PATENT DOCUMENTS

| | | | |
|---|---|---|---|
| 2,705,951 | 4/1955 | Crowner | 128/132 R |
| 3,363,624 | 1/1968 | Fishman | 604/349 |
| 3,759,254 | 9/1973 | Clark | 604/349 |
| 4,354,494 | 10/1982 | Hogin | 604/349 |
| 4,446,860 | 5/1984 | Gutnick | 128/132 R |

Primary Examiner—C. Fred Rosenbaum
Assistant Examiner—Mario Costantino
Attorney, Agent, or Firm—LeRoy Greenspan

[57] ABSTRACT

A condom for use by a male human comprising a phallic-shaped elastic sheath having a closed end and, on the inside surface of said closed end, a local coating adapted for delaying ejaculation by said male during sexual intercourse. The essential ingredient of the local coating may be a local anesthetic. The condom may include a color-coded bump indicating on which side of the sheath the coating is located.

1 Claim, 1 Drawing Sheet

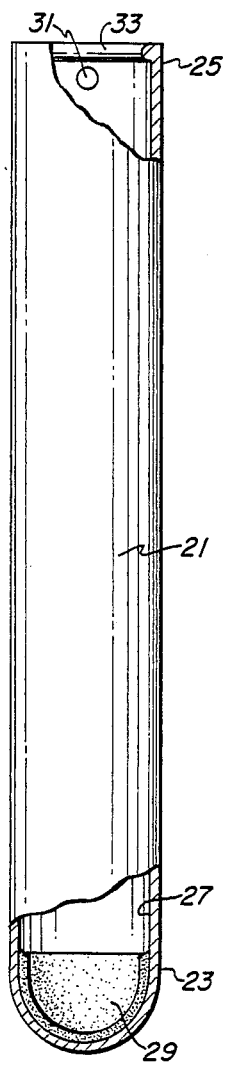
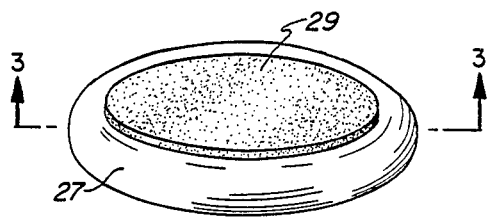
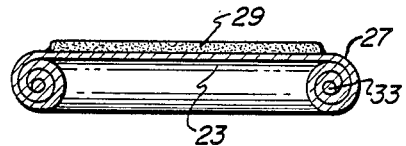
FIG. 1
FIG. 2
FIG. 3

DESENSITIZING CONDOM

BACKGROUND OF THE INVENTION

1. Field of the Invention

This invention relates to a novel configuration of a coated condom for use by a male human during sexual intercourse, and particularly to a novel condom having, on the inner surface thereof, a coating for delaying ejaculation by that male human. By "local coating" is meant a coating over only a limited area of the inner surface.

2. Description of the Prior Art

Sexual dysfunction in humans is now recognized as an increasingly important personal and social problem. One type of sexual dysfunction in male humans is premature ejaculation, which is too short a time interval between entry into the female human and the male orgasm. This results in limited pleasure and some amount of psychological disturbance to the male as well as to the female participant.

Attempts to alleviate or overcome premature ejaculation include counselling; the administration of the therapeutic doses of a pharmaceutical, as described for example in U.S. Pat. Nos. 4,507,323 to W. C. Stern; 4,521,421 to M. M. Foreman; and 4,640,921 to E. Othmer et al; and mechanical devices, such as the device described in U.S. Pat. No. 4,381,000 to L. G. Duncan. Counselling and the administration of pharmaceuticals are both long-term procedures which may require many months to realize a significant effect and in many cases, the procedure may not be effective at all. A mechanical device is awkward to use in the emotional setting for sexual intercourse and requires training and experience to be used efficiently.

A product presently marketed under the trademark MAINTAIN by Schmid Laboratories, Inc., Little Falls, N.J., is a salve which is applied to desensitize the male's penis so as to retard ejaculation. This particular product contains about 7.5% benzocaine in a water-washable base. Such salve should be used with a condom, otherwise the female partner may also be desensitized. Condoms and their manufacture are described in the prior art, for example, in U.S. Pat. No. 4,415,548 to K. P. Reddy. Condoms are packaged dry, or with wet coatings containing lubricant and/or a spermicide. As wtih mechanical devices, it is awkward to use both a salve and a condom in the emotional setting for sexual intercourse. Furthermore, the male must remember to have both the salve and a condom available.

OBJECTS OF THE INVENTION

An object of this invention is to provide a novel condom.

A further object of ths invention is to provide a novel condom which is adapted to delay or prevent premature ejaculation by a male user during sexual intercourse.

Another object of this invention is to provide a novel condom of the type described which can be manufactured economically and used conveniently.

A further object is to provide a novel condom of the type described which can provide an optimum desensitization for the male user, thereby increasing both the pleasure and peace-of-mind of both the participants.

SUMMARY OF THE INVENTION

The novel condom comprised a phallic-shaped elastic sheath having a closed end and, inside the closed end, a local coating for delaying ejaculation by the male participant during sexual intercourse. Preferably, the coating contains, as an essential ingredient, a topical anesthetic such as benzocaine. The novel condom may include a color-coded marking to visually identify the inside surface on which the local coating resides. The novel condom is otherwise similar in its structure and use to prior condoms. However, when properly used, the novel condom can provide an optimum desensitization for the male user, thereby increasing both the pleasure and peace-of-mind of both the participants.

BRIEF DESCRIPTION OF THE DRAWINGS

FIG. 1 is a partially broken-away, elevational view of a first embodiment of the novel condom.

FIGS. 2 and 3 are, respectively, a perspective view and a sectional view of a second embodiment of the novel condom.

DETAILED DESCRIPTION OF THE INVENTION INCLUDING PREFERRED EMBODIMENTS

The following description of some of the preferred embodiments of the concepts of this invention is made in reference to the accompanying figures. Where an individual structural element is depicted in more than one figure, it is assigned a common reference numeral for simplification of identification and understanding.

In general, the novel condom comprises a phallic-shaped elastic sheath (21) having a closed end (23) and an open end (25), as shown in FIG. 1. The inside surface (27) of the sheath (21) over the closed end (23) carries a local coating (29) adapted to delay ejaculation by the male user during sexual intercourse. The local coating (29) contains, as an essential ingredient, a topical anesthetic, such as bezocaine. Other topical anethetics can be used singly or in combination with other anesthetics. The coating may include a water-soluble binder such as polyvinyl alcohol. In one form, the coating (29), comprises pressure-rupturable globules containing the topical anesthetic, which thereby encapsulates the dose of topical anesthetic until the pressure applied during normal use frees the anesthetic.

The inside surface (27) near the open end (25) includes a color-coded marking (31) indicating the surface on which the local coating (29) is located. In that way, the user can redetermine which side of the sheath should be in contact with the male participant during coitus. The color-coded marking may be a small coating of dyed or pigmented material. The open end (25) includes a peripheral ridge (33) cast into the sheath (21). A low bump may also be cast into the inside surface (27) of the sheath (21), and optionally color-coded as a supplemental or alternative side marker.

FIGS. 2 and 3 illustrate an alternative embodiment similar in construction to the embodiment shown in FIG. 1 with exceptions in two important respects. First, the wall of the sheath (21) has been rolled upon itself from the open end (25) towards the closed end (23) to form a torus with the closed end (23) forming a membrane across the torus. In this form, the novel condom can be conveniently unrolled on the male participant as is commonly done. Second, the local coating (29) is placed against the penis of the male user and then unrolled on, ready for use.

The sheath (21) for the novel condom may be prepared by the process disclosed in the above-cited patent to K. P. Reddy. Briefly, a phallic-shaped mandrel of predetermined size and having a circumferential groove is dipped into a warm bath of latex rubber up to the groove, and then is withdrawn, leaving a pinhole-free coating of latex on the mandrel. The latex coating is allowed to cure on the mandrel, thereby forming a sheath having a closed end and an open end with a peripheral ridge. If it is desired to also have a low bump cast into the sheath, the mandrel should also have a low depression at the desired location of the bump. The cured sheath is then rolled up on the mandrel from the open end towards the closed end for form the torus described above. Then the local coating is applied to the membrane across the torus only on the inside surface (27); that is, the surface that was in contact with the mandrel. The coating may be applied using any convenient technique, such as spraying through a stencil or by screening through a stencil. As mentioned above, the coating itself is color coded. Thus, after the coating has dried, the coated condom may be packaged.

The foregoing description and figures are provided as illustrative of some of the preferred embodiments of the concepts of the invention. There are many alternatives in addition to what is disclosed above that fall within the disclosed concepts. While the disclosed embodiments represent what is regarded as the best modes for practicing this invention, they are not intended as delineating of the scope of the invention, which is set forth in the following claims.

What is claimed is:

1. A condom for use by a male human during sexual intercourse comprising a phallic-shaped elastic sheath having a closed end and an open end, a local coating on the inside surface of said closed end, said local coating consisting essentially of a topical anesthetic for delaying ejaculation by saidmale human during said sexual intercourse and a water-soluble base therefor, and a small colored bump on said sheath solely adjacent to said open end, said mark being visually distinct from the color of said sheath and visually indicating said inside surface on which said local coating is located.

* * * * *